United States Patent [19]

Golias et al.

[11] 4,096,825

[45] Jun. 27, 1978

[54] APPARATUS FOR APPLYING AN ORGANIC LIQUID SAMPLE

[75] Inventors: Tipton L. Golias; David Mayes, both of Beaumont, Tex.

[73] Assignee: Helena Laboratories Corporation, Beaumont, Tex.

[21] Appl. No.: 769,977

[22] Filed: Feb. 18, 1977

Related U.S. Application Data

[63] Continuation of Ser. No. 620,736, Oct. 8, 1975, abandoned.

[51] Int. Cl.² ............................................. B05C 1/02
[52] U.S. Cl. .................................. 118/221; 118/243; 118/256; 73/61.1 C
[58] Field of Search ................... 118/9, 54, 243, 256, 118/263, 401, 506, 221; 427/2, 4, 8; 73/61.1 C; 204/299 R, 299 EC

[56] References Cited

U.S. PATENT DOCUMENTS

| | | | |
|---|---|---|---|
| 2,868,020 | 1/1959 | Williams, Jr. | 73/61.1 C |
| 2,902,002 | 9/1959 | Argyle | 118/243 |
| 3,010,427 | 11/1961 | Hautau | 118/243 |
| 3,025,830 | 3/1962 | Vierthaler et al. | 118/243 |
| 3,505,858 | 4/1970 | Kohn | 73/61.1 C |
| 3,616,387 | 10/1971 | Siebert | 73/61.1 C |
| 3,747,397 | 7/1973 | Sharabash | 118/9 X |
| 3,863,599 | 2/1975 | Kohn | 118/256 |

*Primary Examiner*—Mervin Stein

*Attorney, Agent, or Firm*—Cullen, Settle, Sloman & Cantor

[57] ABSTRACT

An apparatus for applying an organic liquid sample such as blood or the like onto an absorbent sample support. The method performed by the apparatus includes the steps of filling a reservoir with a relatively massive sample, superimposing over the reservoir a sample carrier wettable by the sample and to which the sample adheres by surface tension, then immersing the sample carrier into the sample, withdrawing the sample carrier from the reservoir with the sample adhered to the carrier by surface tension, and, contacting the sample carrier with the sample support to break surface tension between the sample and the sample carrier and to deposit the sample onto the sample support.

The apparatus includes a reservoir for receiving a relatively massive sample, a first guide path aligned with the reservoir, and a sample carrier displaceable along said first guide path toward and away from the reservoir with the sample carrier being immersible in the sample. The sample carrier is displaced along the first path to removably immerse the carrier into the sample with the sample adhering to the sample carrier by surface tension. The apparatus also includes a base having a second guide path aligned therewith and the sample carrier is displaced along the second guide path to removably contact the sample carrier with a sample support to break the surface tension between the sample and the sample carrier to deposit the sample on the sample support.

9 Claims, 11 Drawing Figures

U.S. Patent  June 27, 1978  Sheet 1 of 2  4,096,825
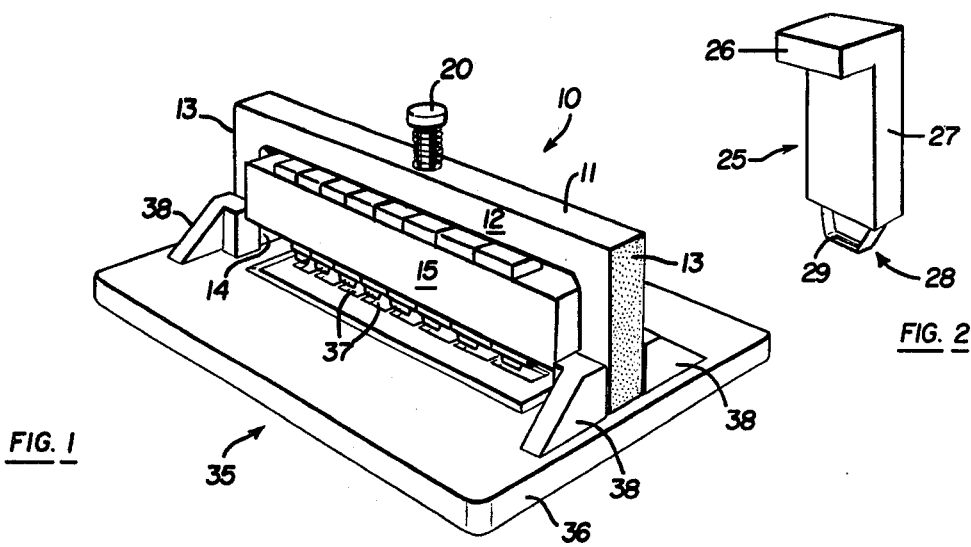
FIG. 1
FIG. 2
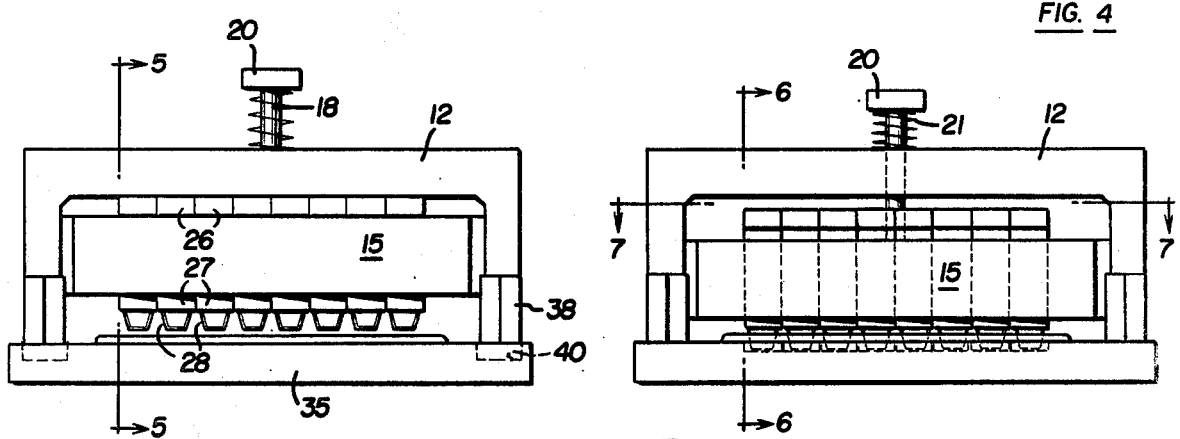
FIG. 3
FIG. 4
FIG. 7
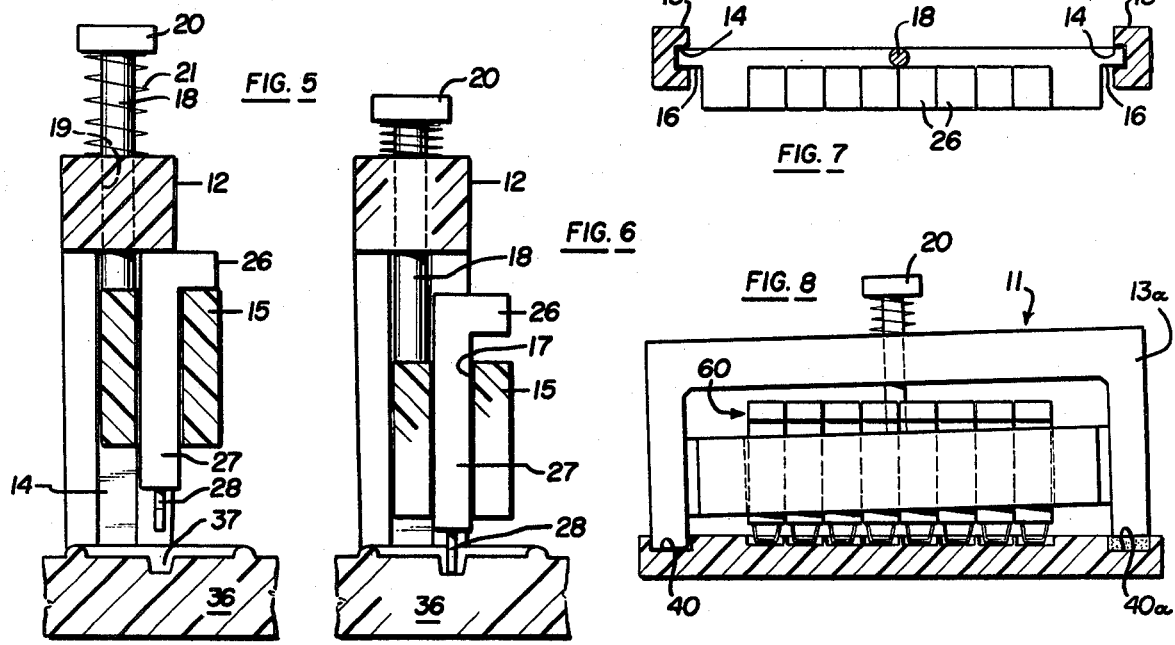
FIG. 5
FIG. 6
FIG. 8

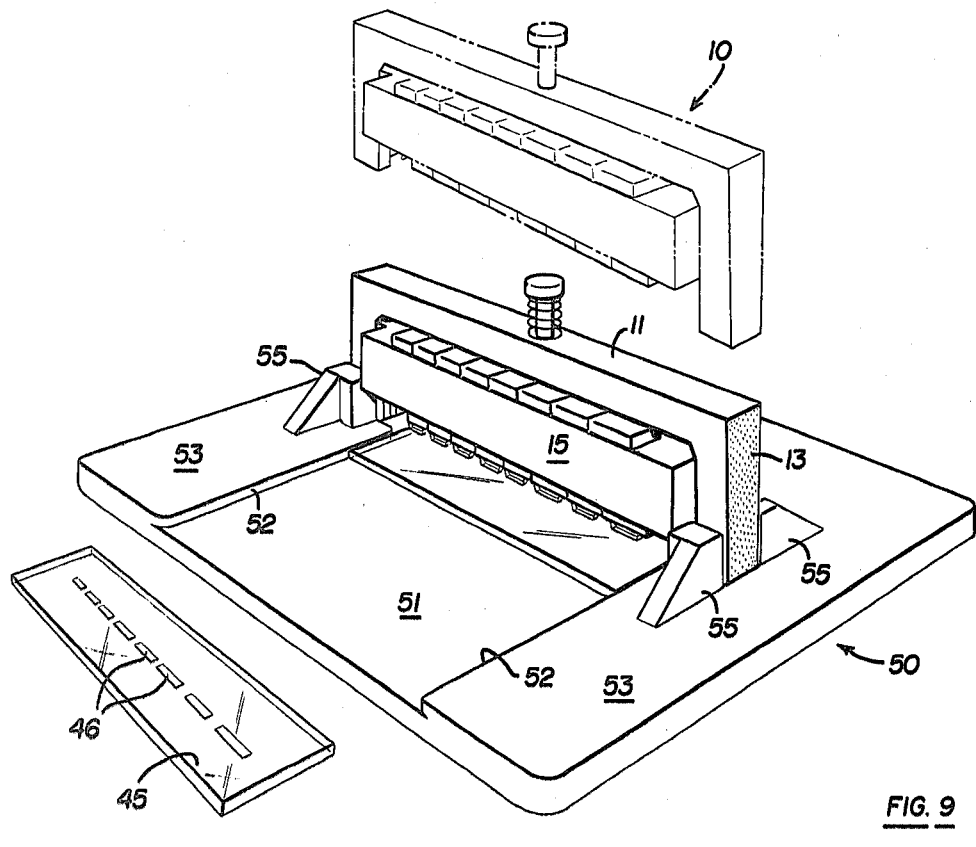
FIG. 9
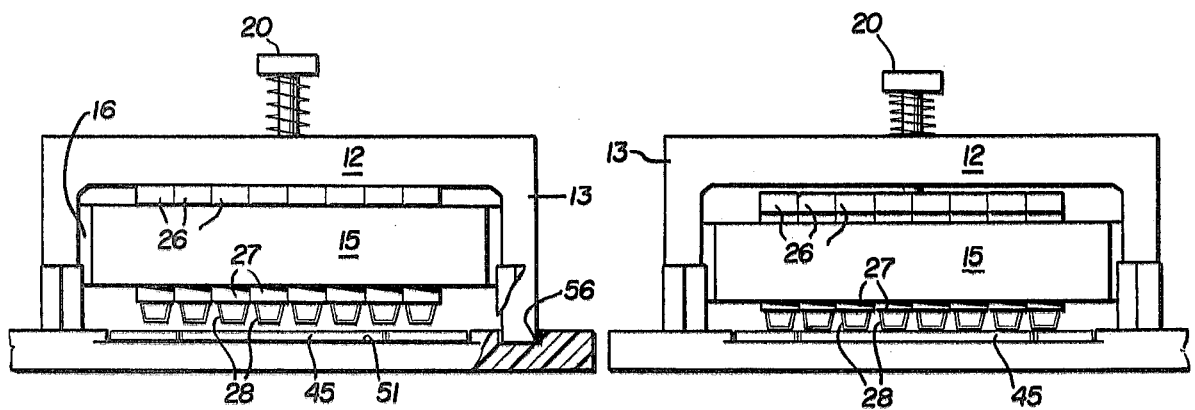
FIG. 10
FIG. 11

APPARATUS FOR APPLYING AN ORGANIC LIQUID SAMPLE

This is a continuation of application Ser. No. 620,736, filed Oct. 8, 1975 and now abandoned.

BACKGROUND OF THE INVENTION

This invention relates in general to an apparatus for transferring uniform samples of an organic liquid, such as blood, onto a support. The present invention has a particular utility in the laboratory in preparing blood samples for subsequent electrophoresis.

In the electrophoresis of blood samples for subsequent processing in a densitometer, it is desirable to be able to rapidly and inexpensively deposit a uniform series of blood samples onto an absorbent support which may be of cellulose acetate.

It is important, in depositing the samples of blood, that they be uniform and substantially independent of the technique of the person preparing the sample. In the prior art, such as U.S. Pat. No. 2,868,020, Williams, issued Jan. 13, 1959, an apparatus is disclosed for applying liquid samples. This apparatus, however, must be manually filled with the sample, such as from an eyedropper or pipette, and thereafter, may be utilized to deposit a single sample onto a sample support such as filter paper.

Thus, the Williams patent, by requiring the hand filling of the sample onto the carrier, does not provide for rapid processing of the blood sample. Furthermore, since electrophoresis requires a series of deposits of the sample, the Williams patent does not assure that each of the deposits of the sample will be uniform. To the contrary, the series of deposits are highly dependent upon the technique of the person preparing and processing the samples.

Finally, the apparatus and method disclosed in the Williams patent does not permit the simultaneous preparation of a series of uniform deposits of the sample to be analyzed.

BRIEF DESCRIPTION OF THE INVENTION

Thus, the present invention is directed to an apparatus for transferring uniform samples of blood or the like onto an absorbent sample support for subsequent processing such as by electrophoresis.

It is, therefore, an object of the present invention to provide an improved method for transferring uniform samples of blood or the like onto an absorbent sample support including filling a reservoir with a relatively massive sample, superimposing over the reservoir a sample carrier wettable by the sample and to which the sample is adherent by surface tension, immersing the sample carrier into the sample to adhere the sample to the carrier, withdrawing the sample carrier from the reservoir with the sample adhered to the carrier and finally, contacting the sample carrier with an absorbent sample support to break the surface tension between the sample and the sample carrier and to deposit the sample onto the sample support.

Yet another object of the present invention is to provide an improved method for transferring a series of uniform samples of blood or the like onto an absorbent support by filling a reservoir with a relatively massive sample, superimposing over the reservoir a plurality of aligned sample carriers, each wettable by the sample and to which the sample is adherent by surface tension, reciprocating the aligned carriers simultaneously relative to the reservoir to immerse the carriers into the sample to adhere the sample to the carriers and to withdraw the carriers from the reservoir with the sample adhered to the carriers, superimposing the series of aligned sample carriers over an absorbent sample support and then simultaneously reciprocating the aligned carriers relative to the absorbent support to break the surface tension between the sample and each of the aligned carriers to deposit the aligned samples onto the sample support.

Yet another object of the present invention is to provide an improved apparatus for transferring uniform samples of blood or the like onto an absorbent sample support including a reservoir for receiving a relative massive sample, first guide means defining a first vertical guide path aligned with the reservoir, a sample carrier displaceable along said first guide path toward and away from said reservoir, said sample carrier being immersible in said sample, said sample carrier being displaceable along said first guide means to removably immerse the carrier into the sample with the sample adhering to the sample carrier by surface tension, a base for receiving a sample support and second guide means defining a second vertical guide path aligned with said base, said sample carrier being displaced along said second guide path to removably contact said sample carrier with a sample support to break the surface tension between the sample and the sample carrier to deposit the samples onto a sample support.

IN THE DRAWINGS

The various objects of the present invention, together with other objects and advantages which may be attained by its use, will become more apparent upon reading the following detailed description taken in conjunction with the drawings.

In the drawings, wherein like reference numerals identify corresponding parts:

FIG. 1 is a perspective illustration of the sample carrier of the present invention aligned with the reservoir of the present invention;

FIG. 2 is an enlarged perspective illustration of one of the elements of the sample carrier;

FIG. 3 is a front elevation view of the sample carrier and reservoir of FIG. 1 with the carrier withdrawn from the reservoir;

FIG. 4 is a front elevation view of the sample carrier and reservoir of FIG. 1 with the carrier immersed in the sample;

FIG. 5 is a cross sectional illustration of the carrier withdrawn from the reservoir as seen in the plane of arrows 5—5 of FIG. 3;

FIG. 6 is a cross sectional illustration of the carrier immersed in the sample as seen in the plane of arrows 6—6 of FIG. 4;

FIG. 7 is a cross sectional illustration of the carrier immersed in the sample as seen in the plane of arrows 7—7 of FIG. 4;

FIG. 8 is a front elevation view of the sample carrier and reservoir of FIG. 1 showing the independent movement of the carrier elements as the carrier is immersed into the reservoir;

FIG. 9 is an exploded perspective illustration of the sample carrier and the base and sample support of the present invention;

FIG. 10 is a front elevation of the sample carrier and base of FIG. 9 with the sample carrier withdrawn from the base; and FIG. 11 is a front elevation of the sample carrier and base of FIG. 9 with the sample carrier contacting the base to deposit the sample.

DETAILED DESCRIPTION OF THE INVENTION

With reference to the drawings, there is illustrated a sample carrier 10 of the present invention including a yoke 11 having an elongated base 12 and opposed parallel downwardly extending legs 13 to define a generally U-shaped configuration. The inwardly facing or opposed sides of the legs 13 are each provided with a vertical longitudinal groove 14 into which is slidably mounted a guide bar 15.

The guide bar 15 is an elongated rectangular bar having outwardly extending side flanges 16 which slide in the grooves 14 in the yoke legs. The guide bar has an elongated slot 17 which extends therethrough from the top to the bottom and extends parallel to the longitudinal dimension of the bar.

In order to actuate the guide bar in the yoke, the guide bar has an upwardly extending stem 18 which may be removably threaded therein at one end and which extends through an aperture 19 in the base 12 of the yoke. The stem has an enlarged cap 20 at its other end and a spring 21 surrounds the stem between the cap 20 and the top of the yoke base 12. Thus, when the carrier is assembled with the guide bar flanges 16 in the grooves 14, the spring resiliently biases the guide bar upwardly toward the yoke base 12.

The carrier is utilized to transfer the blood samples and, for this purpose a plurality of individual applicator elements 25 are independently suspended through the slot 17 of the carrier guide bar. Each applicator element is L-shaped, having a short leg 26 and a long leg 27, as illustrated in greater detail in FIG. 2. When the applicators are suspended in the slot 17 of the guide bar 15 the short leg 26 rests on the top of the guide bar intermediate the guide bar and the yoke base and the long legs 27 extending through the slot 17 in the guide bar and extending below the guide bar 15.

Depending downwardly from the long leg of each applicator 25 is a metallic tip 28 which is generally U-shaped with a slotted base 29. The slotted base forms a rectangular boundary to which the sample adheres by surface tension and in a preferred embodiment, the slot in the base is photoetched. Except for the metal tip 28 and the spring 21, the remaining portions of the carrier 10 may be manufactured of plastic.

The present invention also includes reservoir means 35 into which sample of blood or the like is initially placed. The reservoir means 35 includes a flat base 36 having a plurality of aligned rectangular wells or depressions 37 therein. In order to properly align the carrier on the reservoir means, a pair of opposed vertical guide paths are provided at each side of the reservoir means to receive the legs 13 of the carrier 10. Each guide path includes a pair of legs 38 extending upwardly from the flat base 36 and spaced apart perpendicularly with respect to the axis of the aligned wells. Intermediate the spaced apart legs is a downward recess 40 which extends below the top surface of the flat base 36. The entire reservoir means may be molded of plastic.

According to the principles of the present invention, it is desirable to obtain blood from the reservoir and deposit the blood as aligned, uniform samples on a sample support 45 which may be cellulose acetate strips or even a strip of filter paper. To provide for the uniform deposit of a plurality of aligned samples 46, the present invention includes a generally rectangular, thin, sample support receiving base 50 having a central recessed portion 51 which terminates at its sides into shoulders 52. This defines a guide for the support 45. The portions 53 of the base between the base edges and the shoulders 52 are higher than the recessed central portion 51 of the base.

In order to properly align the carrier over the sample support, the base 50 also includes opposed guide means at each side thereof to define a vertical guide path, with each guide means including a pair of upwardly extending spaced apart legs 55 at each edge of and outwardly of the recessed portion 51 of the base. Each pair of spaced apart legs defines a recess 56 therebetween, which recess extends downwardly to the level of the recessed portion 51 of the base.

The operation of the present invention will now be explained. Initially, the person preparing the blood sample fills the individual wells 37 of the reservoir means 35 with a relatively massive sample. The term "relatively massive" indicates that more blood is deposited into the wells 37 than is to be utilized in the ultimate processing of the blood. The carrier 10 is then superimposed over the reservoir at a filling station by aligning each leg 13 of the carrier between each pair of spaced apart legs 38 of the reservoir means 35. The carrier 10 is superimposed and aligned with the bottoms of each leg 13 extending downwardly into the recesses 40 in the reservoir means.

Next, the carrier 10 is immersed into the reservoir 35 and thereafter, withdrawn from the reservoir with the sample wetting the carrier and adhering to the rectangular boundary 29 of each carrier element by surface tension. Specifically, the cap 20 is depressed and released to reciprocate the guide bar and applicator elements toward and away from the reservoir with the guide bar being reciprocated away from the reservoir by the spring 21. During this reciprocation, each of the metallic tips 28 enters a corresponding well 37 and the sample fills each slotted base 29 by surface tension. This completes the filling of the carrier and the carrier may be removed from the reservoir means 35.

However, during the filling of the carrier 10, it is possible to misalign the carrier 10 relative to the reservoir means 35 as illustrated generally in FIG. 8 where one of the yoke legs 13a has not been inserted and aligned fully in the corresponding recess 40a. When the cap 20 is depressed to immerse the carrier element 28 into the wells, since the applicators themselves are independently suspended in the slotted guide bar, the applicators move different distances until the bottom of each well 37 is contacted by each slotted base 29. Thus, it is seen that the applicators at the left of FIG. 8 have moved a lesser distance, as at 60, then the applicators at the right side of the carrier. However, since the carriers are independently suspended, each applicator tip 28 contacts the bottom of the corresponding well 37 and each slotted base 29 is filled with a sample by surface tension. Thus, the carrier is filled with a sample independent of the alignment technique of the operator.

The carrier 10 is removed from the reservoir means at the filling station and transferred to a depositing station so that the samples may be deposited on a sample support 45, such as the cellulose acetate plate. In order to accomplish this, the sample support is placed on the recessed portion 51 of the base 50 and the carrier is superimposed over the base 50 and aligned with the base by aligning each leg 13 of the carrier yoke between each pair of spaced apart legs 55 of the support base 50, with each yoke leg 13 extending downwardly in a corresponding recess 56.

With the carrier 10 aligned over the support base 50 and with the sample support 45 in place, the cap 20 is again actuated, i.e., depressed and released, to reciprocate the carrier and base 50 toward and away from each other, again with the movement away from each other under the influence of spring 21. This reciprocating movement displaces the carrier relative to the sample support to contact the sample support 45 and to break the surface tension between the sample and the tips 28 of the carriers to deposit a series of aligned uniform samples 46 onto the support 45. Thereafter, of course, the carrier 10 may be removed from its aligned position. Even if the yoke legs 13 are not perfectly aligned in the guides defined between the spaced apart legs 55, since each applicator is independently suspended within the guide bar 15, there is assurance that uniform samples 46 of blood will be deposited on the support 45.

The foregoing explains the principles of the present invention for depositing a series of aligned identical uniform deposits of blood simultaneously. Many changes may be made without departing from the spirit and scope of the present invention. The invention, therefore, should be limited only by the following claims.

What is claimed is:

1. Apparatus for transferring uniform samples of blood or the like onto an absorbent sample support comprising:
   means defining a reservoir for receiving a relatively massive sample;
   first guide means defining a first vertical guide path aligned with said reservoir means;
   a sample carrier vertically displaceable relative to said first guide path toward and away from said reservoir means, said sample carrier being immersible in said sample;
   means for vertically displacing said sample carrier relative to said first guide path to removably immerse said carrier into the sample with the sample adhered to the sample carrier by surface tension;
   a sample support base; and
   second guide means defining a second vertical guide path aligned with said base;
   said sample carrier displacing means also vertically displacing said sample carrier relative to said second guide path to removably contact said sample carrier with a sample support on said sample support base to break the surface tension between the sample and the sample carrier and to deposit the sample on the sample support;
   said sample carrier including a vertically displaceable slide bar having a slot extending therethrough;
   said sample carrier including an applicator element freely suspended from said slide bar and extending through said slot so that upon vertically displacing said sample carrier, said applicator element is vertically displaced solely under the influence of gravity to contact either the sample in said reservoir means when the sample carrier is displaced relative to said first guide means or said sample support when the sample carrier is displaced relative to said second guide means.

2. The invention as defined in claim 1, wherein said reservoir means includes a plurality of discrete wells and wherein said sample carrier includes a plurality of discrete applicator elements aligned with said discrete wells when said sample carrier is displaced along said first guide path; said sample adhering by surface tension to each of said applicator elements.

3. The invention as defined in claim 1, wherein said sample carrier includes a yoke to alternately engage said first and second guide means, said slide bar being slidably mounted on said yoke for vertical movement, said sample carrier having at least one sample applicator element suspended from said slide bar.

4. The invention as defined in claim 3, wherein said sample carrier includes a plurality of sample applicator elements extending through said slot and freely independently suspended from said slide bar.

5. The invention as defined in claim 1, wherein said applicator element includes a metallic tip having a generally rectangular open configuration to form a boundary to which the sample adheres by surface tension.

6. Apparatus for transferring uniform samples of blood or the like onto an absorbent sample support comprising:
   means defining a reservoir for receiving a relatively massive sample;
   first guide means defining a first vertical guide path aligned with said reservoir means;
   a sample carrier vertically displaceable relative to said first guide path toward and away from said reservoir means, said sample carrier being immersible in said sample;
   said sample carrier including a generally U-shaped yoke having an elongated base and terminating in a pair of opposed legs removably engageable with said first guide means, each of said legs having an inwardly facing opposed longitudinal groove therein; said carrier including an elongated slide bar vertically slidable in said grooves parallel to said elongated base and resiliently urged toward said base, said slide bar having an elongated slot extending therethrough; said carrier including an applicator element freely suspended from said slide bar and extending through said slot;
   means for vertically displacing said sample carrier relative to said first guide path to removably immerse said carrier into the sample with the sample adhered to the sample carrier by surface tension;
   a sample support base;
   second guide means defining a second vertical guide path aligned with said base;
   the legs of the yoke of said sample carrier also being removably engageable with said second guide means whereby said sample carrier displacing means also vertically displaces said sample carrier relative to said second guide path to removably contact said sample carrier with a sample support on said sample support base to break the surface tension between the sample and the sample carrier and to deposit the sample on the sample support;
   said applicator element upon vertical displacement of said sample carrier being vertically displaced solely under the influence of gravity to contact either the sample in said reservoir means when the sample carrier is displaced relative to said first guide means or said sample support when the sample carrier is displaced relative to said second guide means.

7. The invention as defined in claim 6, wherein said reservoir means includes a plurality of discrete wells and wherein said sample carrier includes a plurality of discrete applicator elements aligned with said discrete wells when said sample carrier is displaced along said first guide path; said sample adhering by surface tension to each of said applicator elements.

8. The invention as defined in claim 6, wherein said sample carrier includes a plurality of sample applicator elements extending through said slot and freely independently suspended from said slide bar.

9. The invention as defined in claim 6, wherein said applicator element includes a metallic tip having a generally rectangular open configuration to form a boundary to which the sample adheres by surface tension.

* * * * *